United States Patent
Spencer (10) Patent No.: US 12,419,573 B2
(45) Date of Patent: Sep. 23, 2025

(54) MOUTH-OPENING MEASURING DEVICE

(71) Applicant: David Spencer, Manton, MI (US)

(72) Inventor: David Spencer, Manton, MI (US)

( * ) Notice: Subject to any disclaimer, the term of this patent is extended or adjusted under 35 U.S.C. 154(b) by 518 days.

(21) Appl. No.: 17/966,760

(22) Filed: Oct. 14, 2022

(65) Prior Publication Data

US 2023/0124570 A1 Apr. 20, 2023

Related U.S. Application Data (60) Provisional application No. 63/255,676, filed on Oct. 14, 2021.

(51) Int. Cl.
*A61B 5/107* (2006.01)
*A61B 5/00* (2006.01)
*A61B 5/11* (2006.01)

(52) U.S. Cl.
CPC .......... *A61B 5/4542* (2013.01); *A61B 5/1121* (2013.01); *A61B 5/7455* (2013.01)

(58) Field of Classification Search
CPC ..... A61B 5/107; A61B 5/1071; A61B 5/1072; A61B 5/1076; A61B 5/1121; A61B 5/4542; A61B 5/7455
USPC .................................................. 33/513, 514
See application file for complete search history.

(56) References Cited

U.S. PATENT DOCUMENTS

| | | | | |
|---|---|---|---|---|
| 4,843,720 A * | 7/1989 | Kim | ........................ | G01B 3/20 33/513 |
| 4,997,368 A | 3/1991 | Mayer et al. | | |
| 5,154,609 A * | 10/1992 | George | ................ | A61C 9/0006 433/68 |
| 5,361,506 A | 11/1994 | Beeuwkes, III | | |
| 5,584,125 A * | 12/1996 | Prete | ..................... | A61M 16/06 33/501.45 |
| 5,685,084 A * | 11/1997 | Demers | .................. | A61C 19/04 33/513 |
| 7,144,251 B1 * | 12/2006 | Karapetyan | ............ | A61C 19/04 33/513 |
| 7,954,251 B2 * | 6/2011 | Nunes | .................. | A61B 5/1076 33/514 |
| 8,347,517 B2 * | 1/2013 | Polei | ...................... | G01B 3/563 33/514 |
| 10,307,233 B1 * | 6/2019 | Davydov | ................ | A61C 11/00 |
| 10,925,809 B2 * | 2/2021 | Sieffert | ............... | A61M 13/003 |
| 11,129,680 B2 * | 9/2021 | Shelton, IV | ........... | A61B 34/20 |
| 2013/0273502 A1 * | 10/2013 | Shaw | ..................... | A61C 15/02 132/322 |
| 2015/0126873 A1 * | 5/2015 | Connor | ................ | A61B 5/6887 600/407 |
| 2019/0076226 A1 | 3/2019 | Clauss | | |
| 2021/0145316 A1 * | 5/2021 | Groman | ................ | A61B 5/1072 |
| 2024/0299131 A1 * | 9/2024 | Hultgren | ................ | A61C 7/002 |

FOREIGN PATENT DOCUMENTS

| EP | 3040049 B1 | 8/2020 |
|---|---|---|
| EP | 3448305 B1 | 12/2020 |
| GB | 2494232 A | 7/2012 |

* cited by examiner

*Primary Examiner* — George B Bennett
(74) *Attorney, Agent, or Firm* — Traverse Legal, PLC (57) ABSTRACT

A mouth-opening measuring device includes a first end and an opposing second end. The width of the first end is less than the width of the second end such that the different widths on the first and second ends provide for different mouth opening abilities of an individual when either the first end or the second end is inserted into an individual's mouth.

9 Claims, 9 Drawing Sheets

MOUTH-OPENING MEASURING DEVICE

CROSS-REFERENCE TO RELATED CASES

This patent application claims priority to U.S. Provisional Patent Application No. 63/255,676, filed Oct. 14, 2021, entitled "Mouth-Opening Measuring Device", the disclosure of which is incorporated herein by reference in its entirety.

FIELD

This disclosure relates generally to measuring devices and, more particularly, to a device for measuring the amount of mouth-opening between an upper jaw and a lower jaw of an individual.

BACKGROUND

A number of diseases, conditions, and ailments may limit the extent to which a person can open their mouth. This limit may be a direct result of the physical problem, caused indirectly, or as a result of a surgical procedure, including dental work. During pre- and post-operative examinations of an individual who has undergone or may undergo certain facial procedures or oral surgery, it is vital to be able to assess the amount of mobility of an individual's upper jaw (mandible) and/or lower jaw (maxilla), as determined by the size of the individual's mouth opening.

However, existing devices for measuring an individual's mouth opening fail to provide accurate and reliable measurements of an individual's mouth opening. Also, existing devices may not be easily used by an individual (by themselves) since existing devices do not allow an individual to readily open his/her mouth to insert the device. Further, existing devices for measuring an individual's mouth may become inadvertently lodged in an individual's mouth.

Consequently, there is a need for a device that can provide more precise and accurate measurement of an individual's mouth opening, while also allowing the individual to pry open their mouth in order to insert and safely use the device.

BRIEF SUMMARY

In one embodiment, a measuring device is disclosed for measuring an individual's mouth opening between an upper jaw and a lower. The measuring device includes a first end and an opposing second end, wherein the first end exhibits a width that is less than the width of the second end. The measuring device also includes a plurality of engagement members, each configured to be engaged with a tooth on the upper jaw and/or a tooth on the lower jaw, wherein each of the engagement members includes an inner surface and an outer surface. The measuring device includes a measuring surface positioned between and connected with first and second engagement members. The measuring surface includes a plurality of measurement values. The measuring device further includes a plurality of tactile feel regions disposed along the outer surfaces of each of the engagement members, wherein the tactile feel regions are adjacent to and associated with corresponding measurement values on the measuring surface.

In one embodiment, the device includes two or more engagement portions extending lengthwise thereon, wherein each of the engagement portions includes an outer surface. The device also includes a measuring surface positioned between and linking at least two engagement portions. The measuring surface includes numerical measurements extending lengthwise thereon, wherein the lowest measurements are on the ends of the measuring surface. The device also includes a plurality of notches positioned on each of the outer surfaces of the engagement portions. The notches are associated with specific measurements on the measuring surface.

In one embodiment, the device also includes two extending members that interact with and that are substantially perpendicular to the engagement portions. The extending members may be located at approximately the center of the device and serve to prevent the device from inadvertently slipping further into an individual's mouth.

In one embodiment, the device also includes two extending members that interact with and that are substantially perpendicular to the engagement portions. The extending members may be located at approximately the center of the device and serve to prevent the device from inadvertently slipping further into an individual's mouth.

BRIEF DESCRIPTION OF THE DRAWINGS

The appended drawings illustrate only exemplary embodiments of the invention and therefore do not limit its scope because the inventive concepts lend themselves to other equally effective embodiments.

DETAILED DESCRIPTION

It is to be understood that the present disclosure may assume various alternative orientations and step sequences, except where expressly specified to the contrary. It is also understood that the specific devices and processes illustrated in the attached drawings, and described in the specification are simply exemplary embodiments of the inventive concepts disclosed and defined herein. Hence, specific dimensions, directions or other physical characteristics relating to the various embodiments disclosed are not to be considered as limiting, unless expressly stated otherwise.

Directional terms, such as "top". "bottom", "front". "back", "inwards" "upwards", "downwards", "perpendicular", "parallel" and "laterally" are used in following detailed description for the purpose of providing relative reference only, and are not intended to suggest any limitations on how any article is to be positioned during use, or to be mounted in an assembly or relative to an environment.

REPRESENTATIVE COMPONENT LIST

The following component list is provided as a convenience to the reader. The disclosed technology is not limited to only these representative components that are recited below for purposes of example and convenience for the reader.

12—first end
14—second end
16—first engagement portion
16A—outer surface
18—second engagement portion
18A—outer surface
20—third engagement portion
20A—outer surface
22—fourth engagement portion
22A—outer surface
24—two radially extending members
26—measuring surface
28—tactile feel regions
30—holes
100—user
102—hand
104—mouth FIGS. 1-9 show views of a mouth-opening measuring device 10 according to one embodiment of the present disclosure. The device 10 is configured to measure the amount of mouth-opening between an individual's upper jaw and lower jaw and to gradually and safely increase an individual's jaw opening. More specifically, the device 10 is used for measuring a distance between an individual's teeth (such as front teeth) in the lower jaw and teeth (such as front teeth) in the upper jaw as a mouth-opening amount. Also, the device 10 allows an individual to improve their ability to gradually open their jaw opening by allowing increasing portions of the device 10 to be inserted therein over time.

Mouth-opening measuring device 10 may be used by a medical practitioner as part of an examination treatment and can also be self-administered. Device 10 is lightweight and compact allowing it to be portable and easily stored in a user's pocket. Lightweight materials such as plastic may be employed to fabricate device 10 using molding processes.

Figure 1:
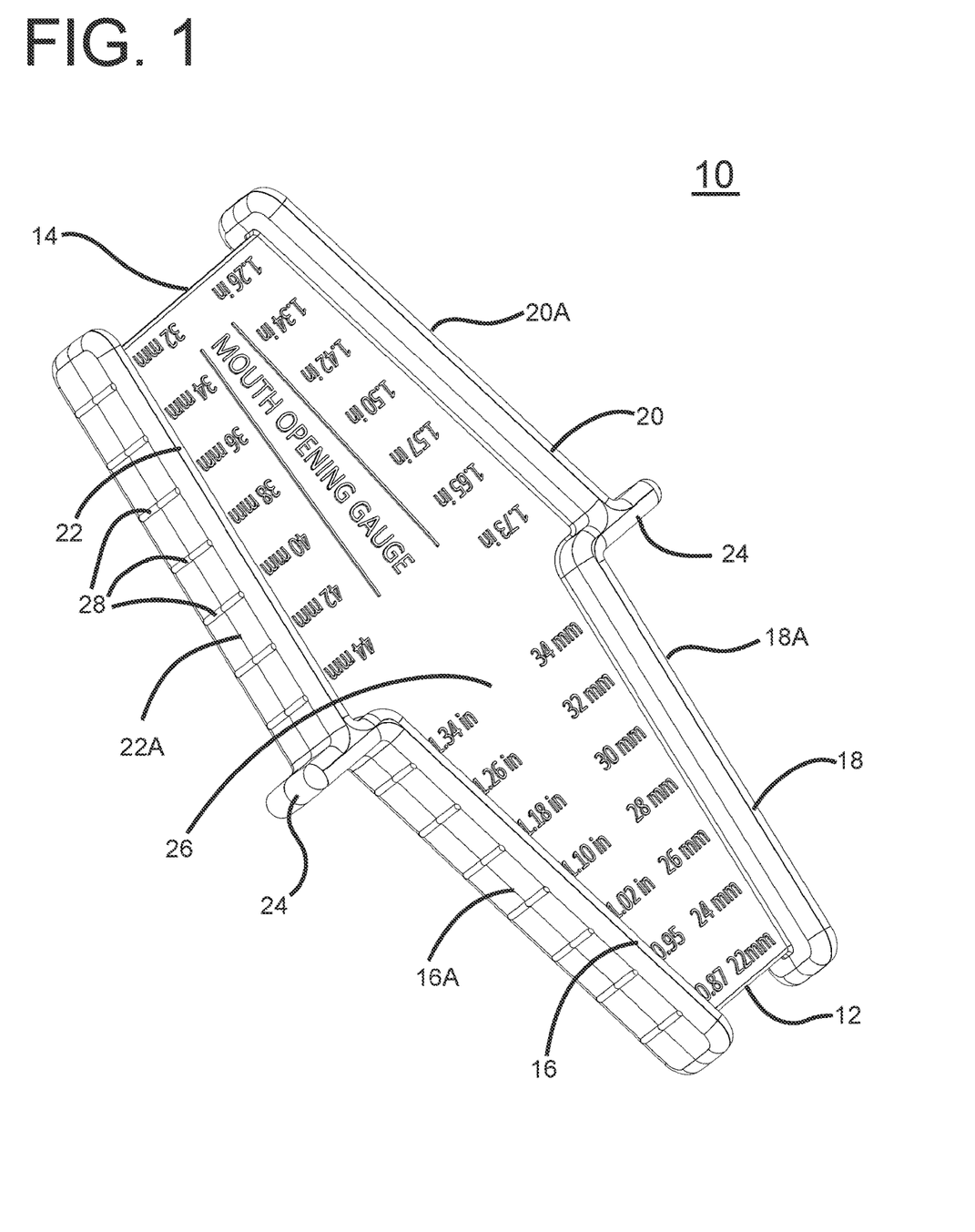
FIG. 1 shows a front perspective view of one embodiment of the disclosed mouth-opening measuring device.
Figure 2:
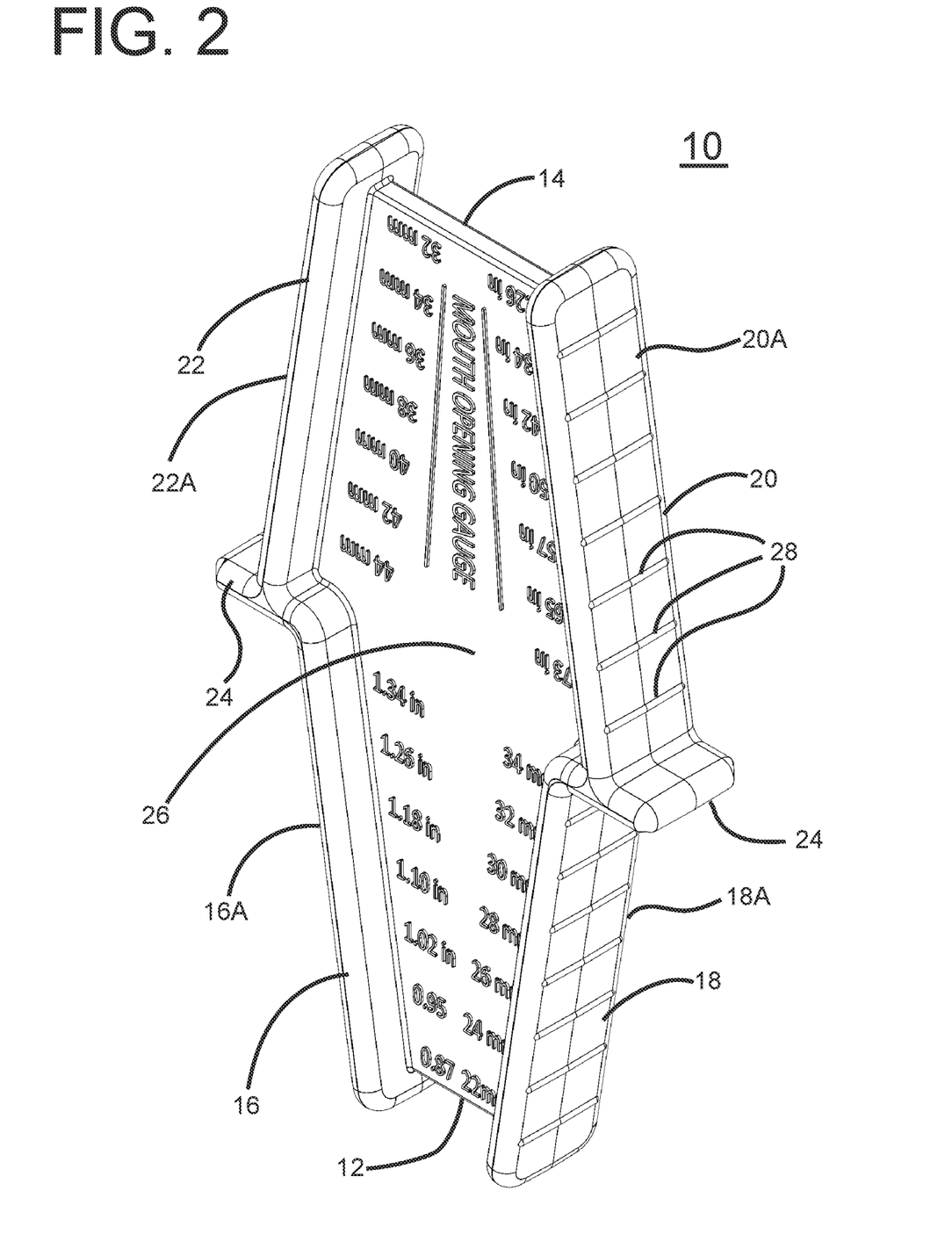
FIG. 2 shows a perspective view of the embodiment of the mouth-opening measuring device of FIG. 1 oriented vertically.
Figure 3:
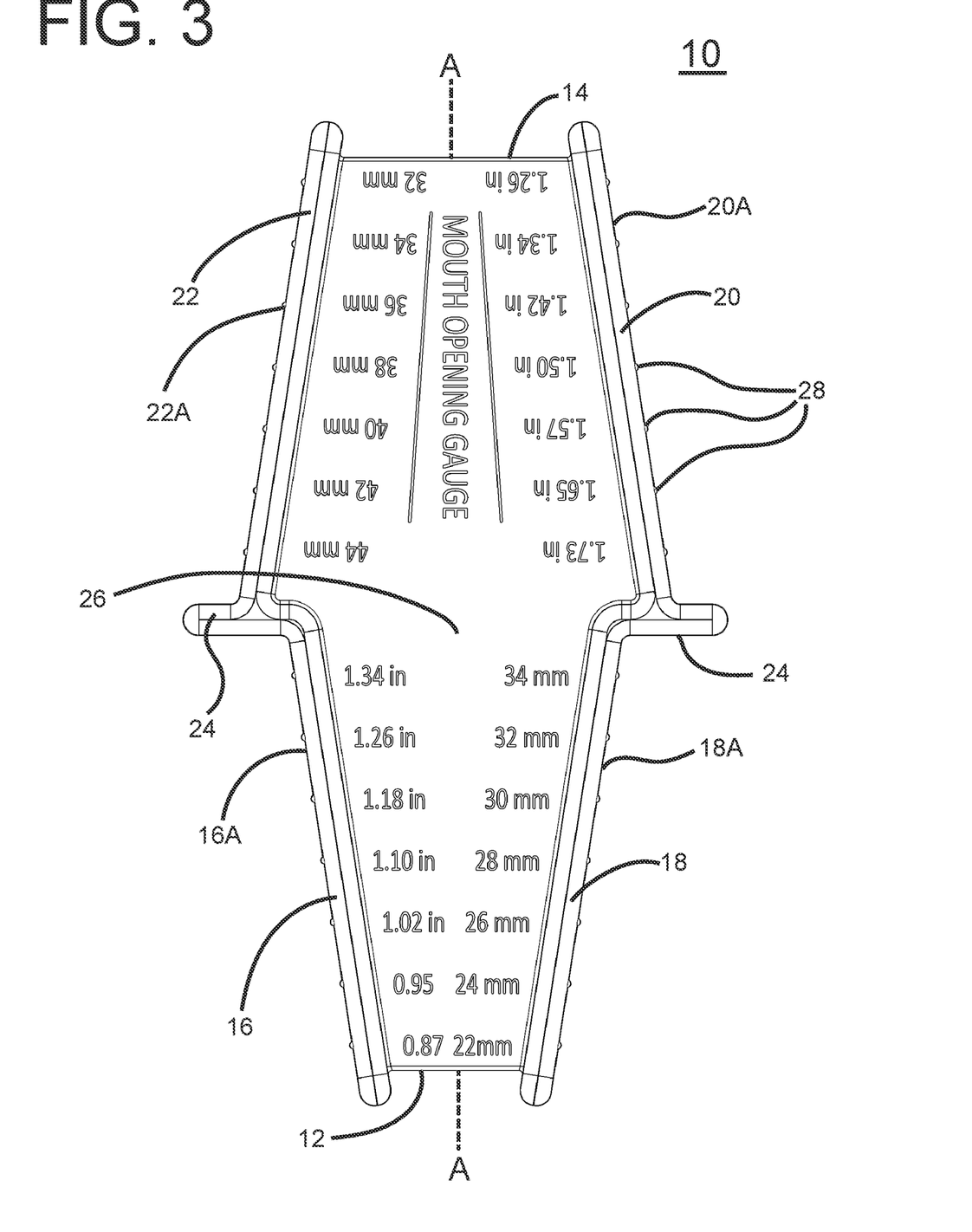
FIG. 3 shows a front plan view of one embodiment of the disclosed mouth-opening measuring device.

As best seen in FIGS. 1-3, mouth-opening measuring device 10 includes a first end 12 and an opposing second end 14, wherein the width of the first end 12 is less than the width of the second end 14. The different widths on the first and second ends 12, 14 provide for different mouth opening abilities of an individual when either the first end 12 or the second end 14 is inserted into an individual's mouth. An individual who is unable to open their mouth very much (i.e. less than about 1.25 inches/32 millimeters) will likely start by inserting the narrower first end 12 into the mouth. An individual who is able to open their mouth at least about 1.25 inches/32 millimeters will likely use the wider second end 14 for mouth insertion.

As seen in FIGS. 1-3, device 10 includes a first engagement portion 16 and an opposing second engagement portion 18 on the first end 12, and a third engagement portion 20 and an opposing fourth engagement portion 22 on the second end 14. In this embodiment, all of engagement portions 16, 18, 20, 22 are raised surfaces that are configured to engage with an individual's upper and lower teeth during use of mouth-opening measuring device 10.

The first and second engagement portions 16, 18 extend lengthwise from about the middle of device 10 toward the first end 12 and the third and fourth engagement portions 20, 22 extend lengthwise from about the middle of the device 10 toward the second end 14. The first and second engagement portions 16, 18 angle inward toward the first end 12 such that the distance between the first and second engagement portions 16, 18 is the shortest at the first end 12. Similarly, the third and fourth engagement portions 20, 22 curve inward toward the second end 14 such that the distance between the third and fourth engagement portions 20, 22 is the shortest at the second end 14. First and second engagement portions 16, 18 exhibit a V-like geometry wherein the vertex of the V is truncated. Likewise, in this particular embodiment, third and fourth engagement portions 20, 22 exhibit a V-like geometry wherein the vertex of the V is truncated.

As best seen in FIGS. 1-5, and as a non-limiting example, the device 10 includes two radially extending members 24 positioned at about the middle of the device 10. Each of the engagement portions 16, 18, 20, 22 is linked with one of the extending members 24 such that the extending members 24 are substantially perpendicular to the engagement portions 16, 18, 20, 22. In one embodiment seen in FIG. 3, device 10 includes a longitudinal axis A-A and extending members 24 are substantially perpendicular to longitudinal axis A-A. In one embodiment, the first and second engagement portions 16, 18 intersect the extending members 24 closer to the center of the device 10 than where the third and fourth engagement portions 20, 22 intersect with the extending members 24.

The extending members 24 are configured to stop the device 10 from inadvertently slipping/falling further into an individual's mouth by resting against the sides of an individual's mouth when the device 10 is in operation. Specifically, the extending members 24 ensure that an individual does not close their mouth with the device 10 inside.

As best seen in FIGS. 1-3, the device 10 also includes a substantially planar measuring surface 26 positioned between the engagement portions 16, 18, 20, 22. Portions of the first and second engagement portions 16, 18 extend beyond an end of the measuring surface 26 on the first end 12 and portions of the third and fourth engagement surfaces 20, 22 extend beyond an end of the measuring surface 26 on the second end 14. The measuring surface 26 extends lengthwise between the first and second ends 12, 14 such that it is also inserted into an individual's mouth during operation of the device 10.

As best seen in FIG. 3, the measuring surface 26 includes measurements (e.g. 34 mm, 32 mm, 30 mm, . . . ) identified at predetermined intervals along its length for measuring the mouth opening distance of individuals. The measurements are provided lengthwise along the measuring surface 26 starting from each of the first end 12 and the second end 14. In the embodiment disclosed herein, the measurements correspond to and are adjacent to each of the engagement portions 16, 18, 20, 22, wherein the lowest measurements are closest to each of the first and second ends 12, 14 and the highest measurements are closest to the extending members 24 at about the middle of device 10.

In the embodiment of the device 10 shown herein, the measurements are provided in both inches and millimeters on the measuring surface 26. For example, the measurements in inches may be provided next to the first and third engagement portions 16, 20, while the measurements in millimeters may be provided next to the second and fourth engagement portions 18, 22. In other embodiments, the measurements may be provided in just inches, in just millimeters, or in any other commonly used measuring units.

In the embodiment of the device 10 shown herein, the values of the measurements closest to the first end 12 range from about 0.87 inches (corresponding to about 22 millimeters) to about 1.34 inches (corresponding to about 34 millimeters). In the embodiment of the device 10 shown herein, the values of the measurements closest to the second end 14 range from about 1.26 inches (corresponding to about 32 millimeters) to about 1.73 inches (corresponding to about 44 millimeters). In this embodiment, each of the values on the measuring surface 26 increases gradually by about 0.8 inches/2 millimeters. One of ordinary skill in the art would understand that the values of the measurements and the transitions of the values may vary in other embodiments.

As best seen in FIGS. 1 and 3 and as a non-limiting example, each of the engagement portions 16, 18, 20, 22 includes outer surfaces 16A, 18A, 20A, 22A, respectively, on the left and right sides of the device 10. Each of the outer surfaces 16A, 18A, 20A, 22A includes tactile feel regions 28 that serve as scale markers associated with the respective values displayed on the measuring surface 26 that are directly adjacent to the notches 28. The values displayed on the measuring surface 26 correspond to the width between outer surface 16A and outer surface 18A at a specific point along the engagement portions 16, 18, 20, 22. Tactile feel regions 28 may be notches in the surface of engagement portions or raised portions (e.g. bumps) in the surface of the engagement portions such that the user can feel the location of the notch/bump to help ascertain the corresponding distance reading associated with the particular tactile feel region.

More particularly, the tactile feel regions (e.g. notches) 28 on the outer surfaces 16A, 18A, 20A, 22A can be easily felt by a user's finger in order to easily and quickly determine the corresponding distance values associated with the extent that an individual's mouth is opened. Due to the number and gradual transition of the notches 28, an individual's mouth opening may be precisely and accurately measured. For example, there are 7 notches 28 on each of the outer surfaces 16A, 18A, 20A, 22A of the device 10 disclosed herein. Other embodiments may include either more than 7 or fewer than 7 notches on other mouth-opening measuring devices. Thus, there is a one-to-one correspondence between the number of tactile feel regions (notches) 28 and distance measurements.

The shape and configuration of the device 10 disclosed herein provides for more accurate and improved measurements of mouth opening, while preventing the device 10 from slipping further into an individual's mouth.

As seen in FIGS. 1-5, regions on the first and second engagement portions 16, 18 extend beyond the first end 12 and regions on the third and fourth engagement portions 20, 22 extend beyond the second end 14. These regions on the engagement portions 16, 18, 20, 22 allow an individual to safely and easily pull open their mouths, by themselves, to more easily insert the device 10 therein. This is particularly important for individuals that have very limited range of movement in their jaws. Also, this allows for helping to train various jaw muscles in order to increase mouth opening ability over time with continued use.

Figure 4:
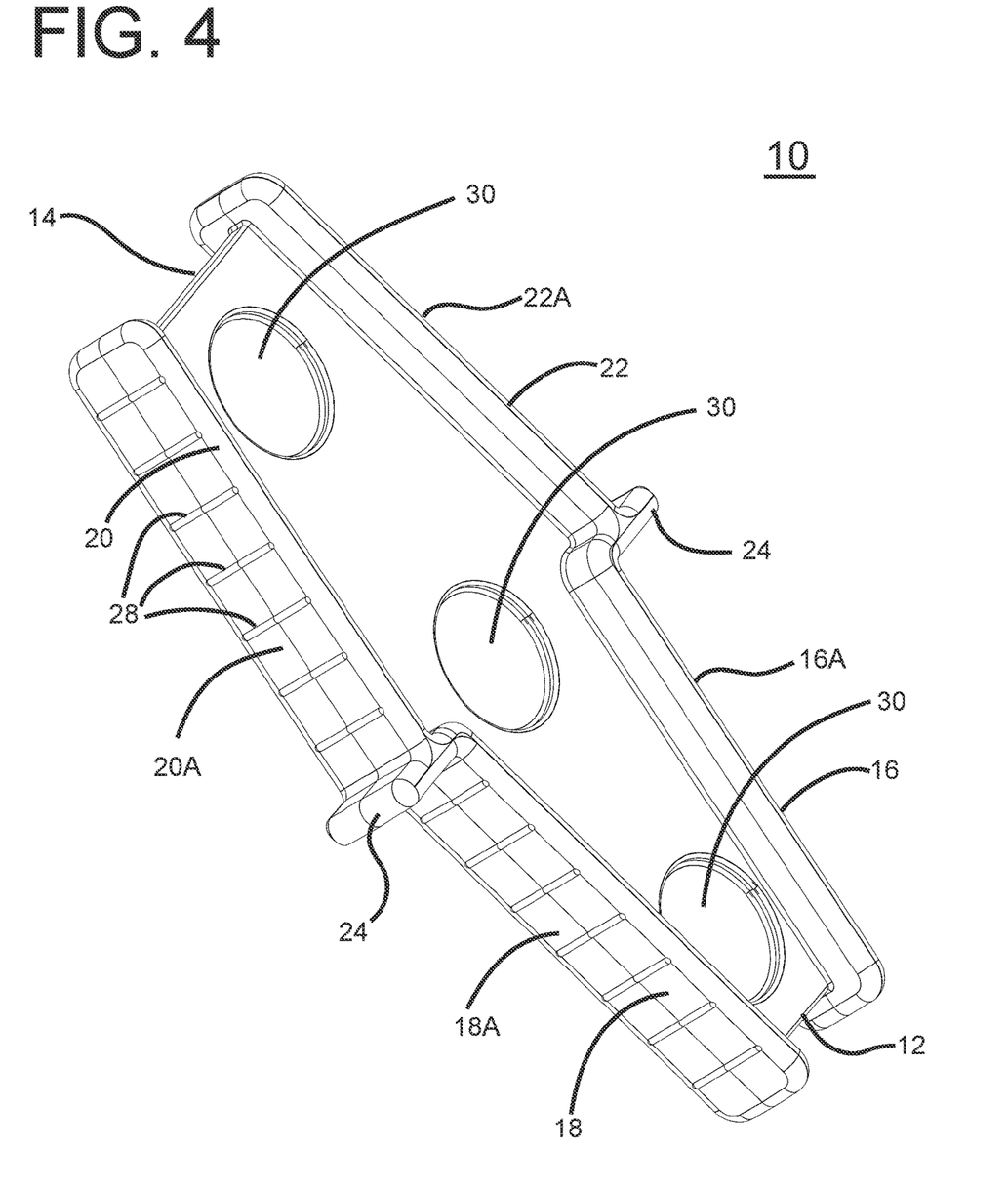
FIG. 4 shows a back perspective view of the embodiment of the disclosed mouth-opening measuring device of FIG. 1.
Figure 5:
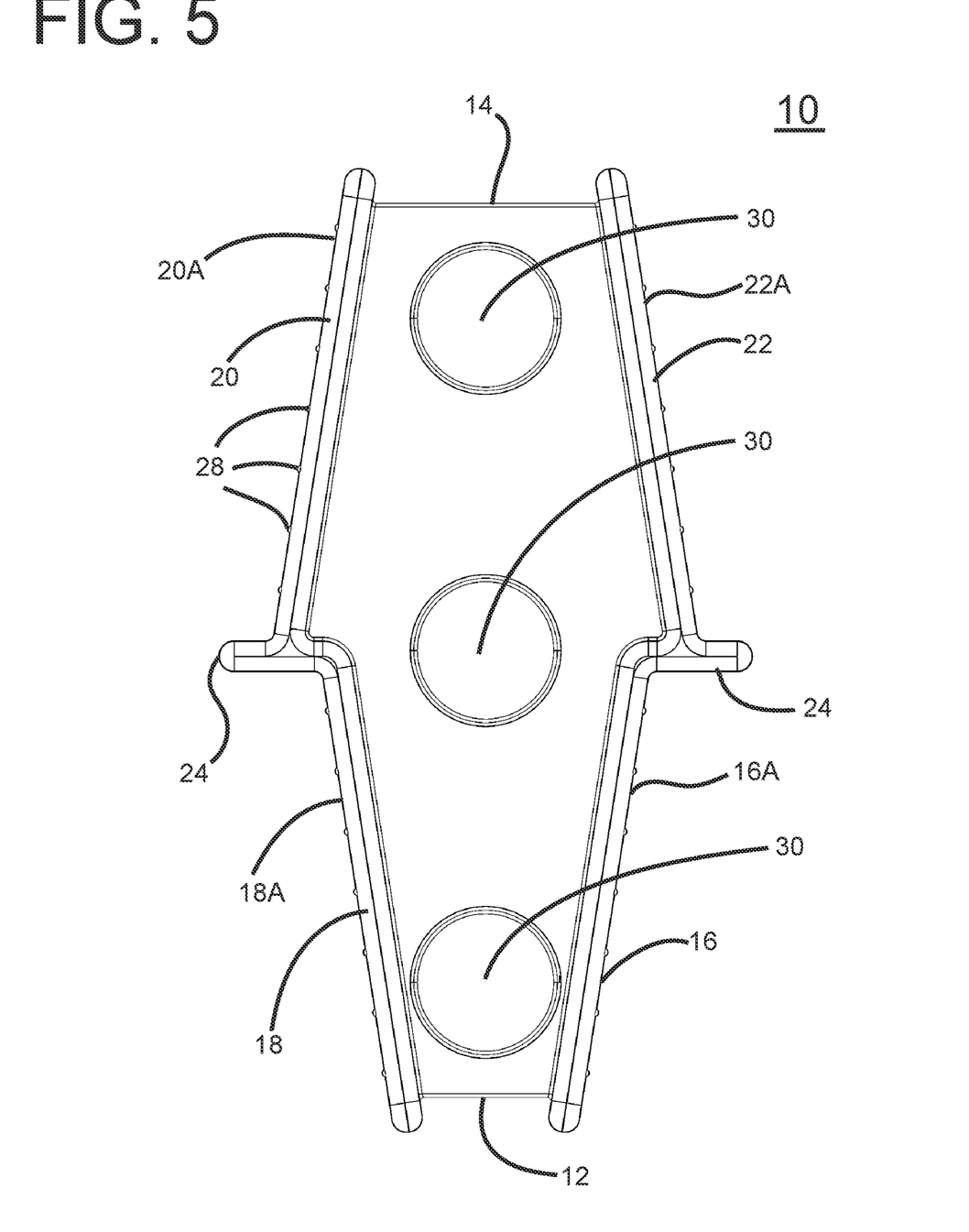
FIG. 5 shows a back plan view of the embodiment of the disclosed mouth-opening measuring device of FIG. 1

As best seen in FIGS. 4 and 5, as a non-limiting example, the back or rear side of the device 10 includes a plurality of spaced-apart holes 30. One or more of the holes 30 are adapted to be used as handles for placement of fingers (e.g. thumbs) therein. In the embodiment shown in FIG. 5, the upper and lower holes 30 are adapted as handles for thumbs to allow individuals to more easily manipulate and insert the device 10 into their mouths. It is noted that in one embodiment, holes 30 do not extend all the way through device 10 to the opposite front side of device 10. In this embodiment, holes 30 extends part way through device 10 to avoid interfering with the measurement information on the measuring surface 26 on the front side of device 10.

Figure 6:
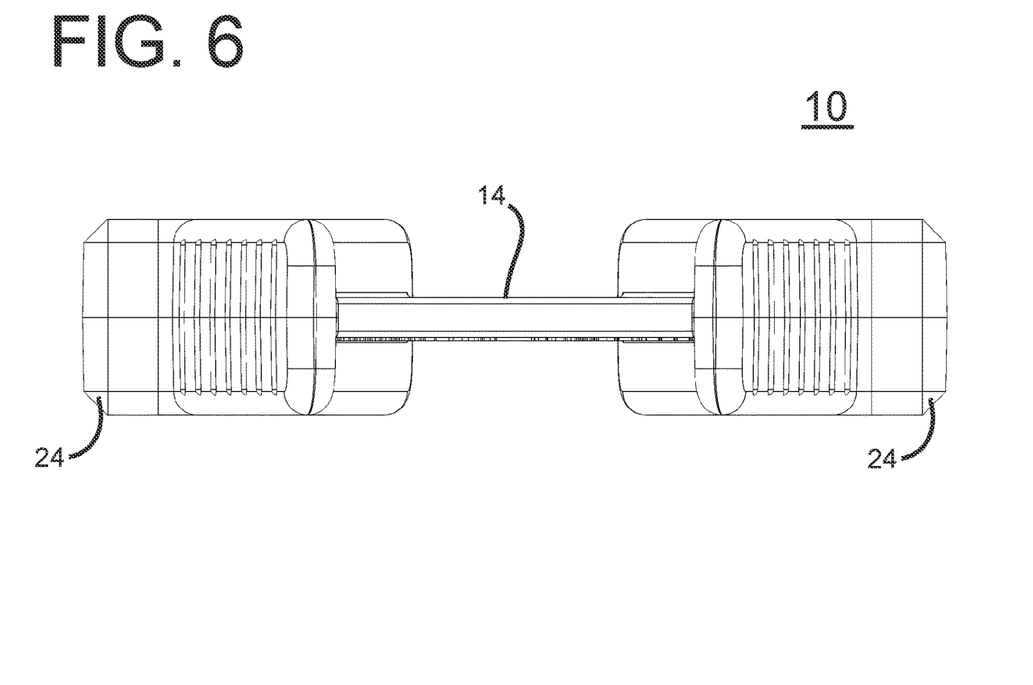
FIG. 6 shows a top plan view of the embodiment of the disclosed mouth-opening measuring device of FIG. 1.
Figure 7:
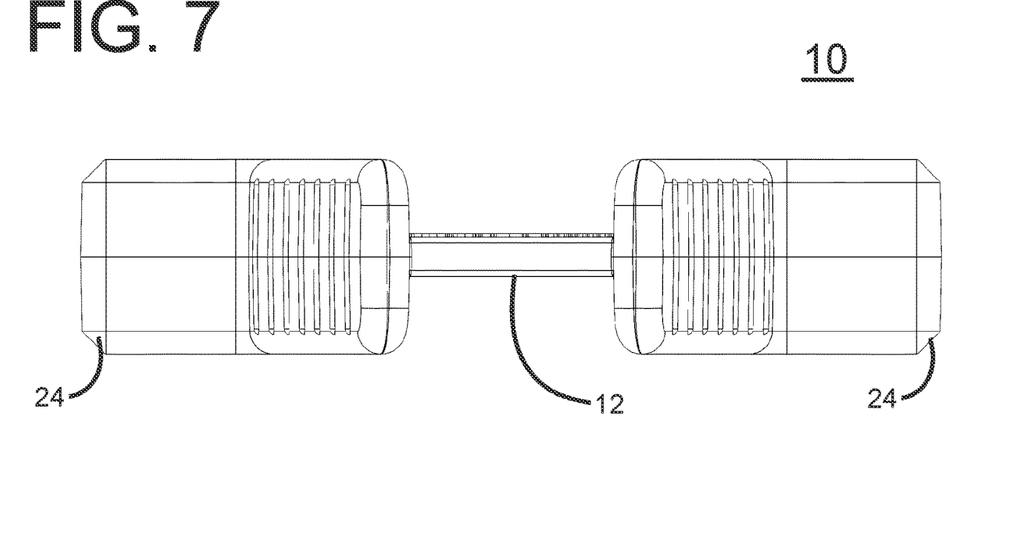
FIG. 7 shows a bottom plan view of the embodiment of the disclosed mouth-opening measuring device of FIG. 1.
Figure 8:
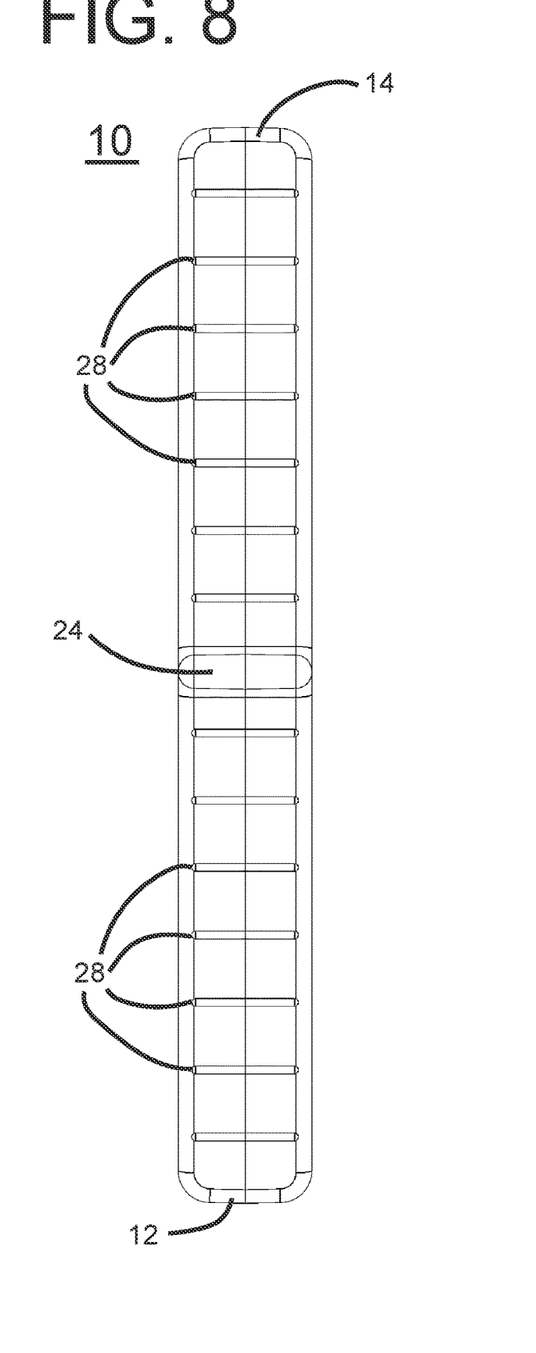
FIG. 8 shows a left side plan view of the embodiment of the disclosed mouth-opening measuring device of FIG. 1.
Figure 9:
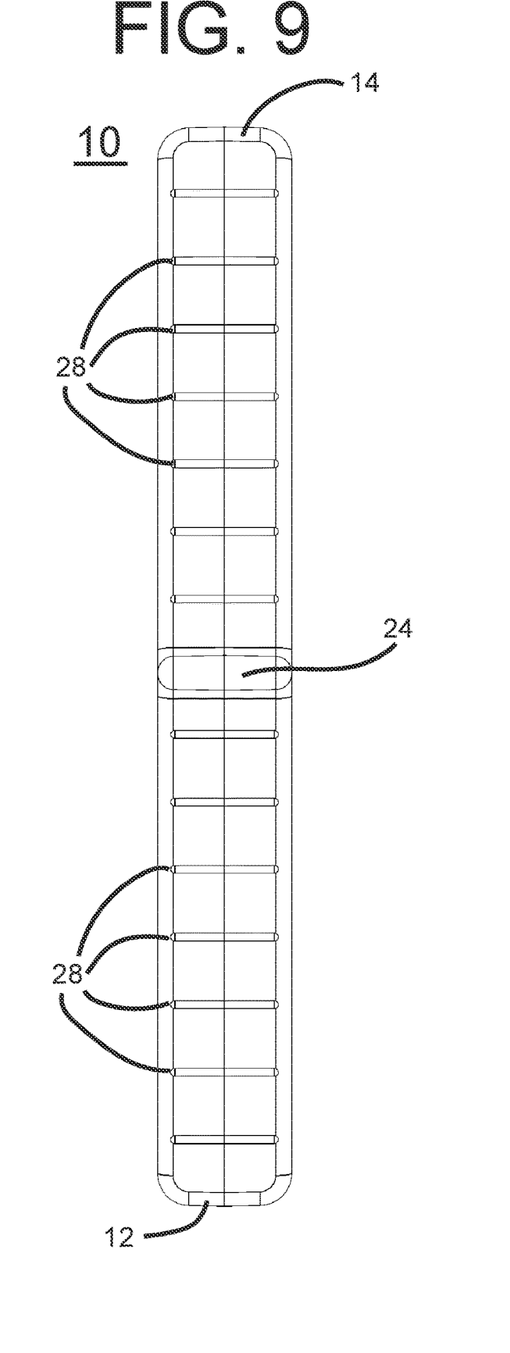
FIG. 9 shows a right side plan view of the embodiment of the disclosed mouth-opening measuring device of FIG. 1.

FIG. 6 shows a top plan view of device 10 looking down at end 14, while FIG. 7 shows a bottom plan view of device 10 looking up at end 12. FIG. 8 shows a left side plan view of device 10, while FIG. 9 shows a right side plan view of device 10.

Figure 10:
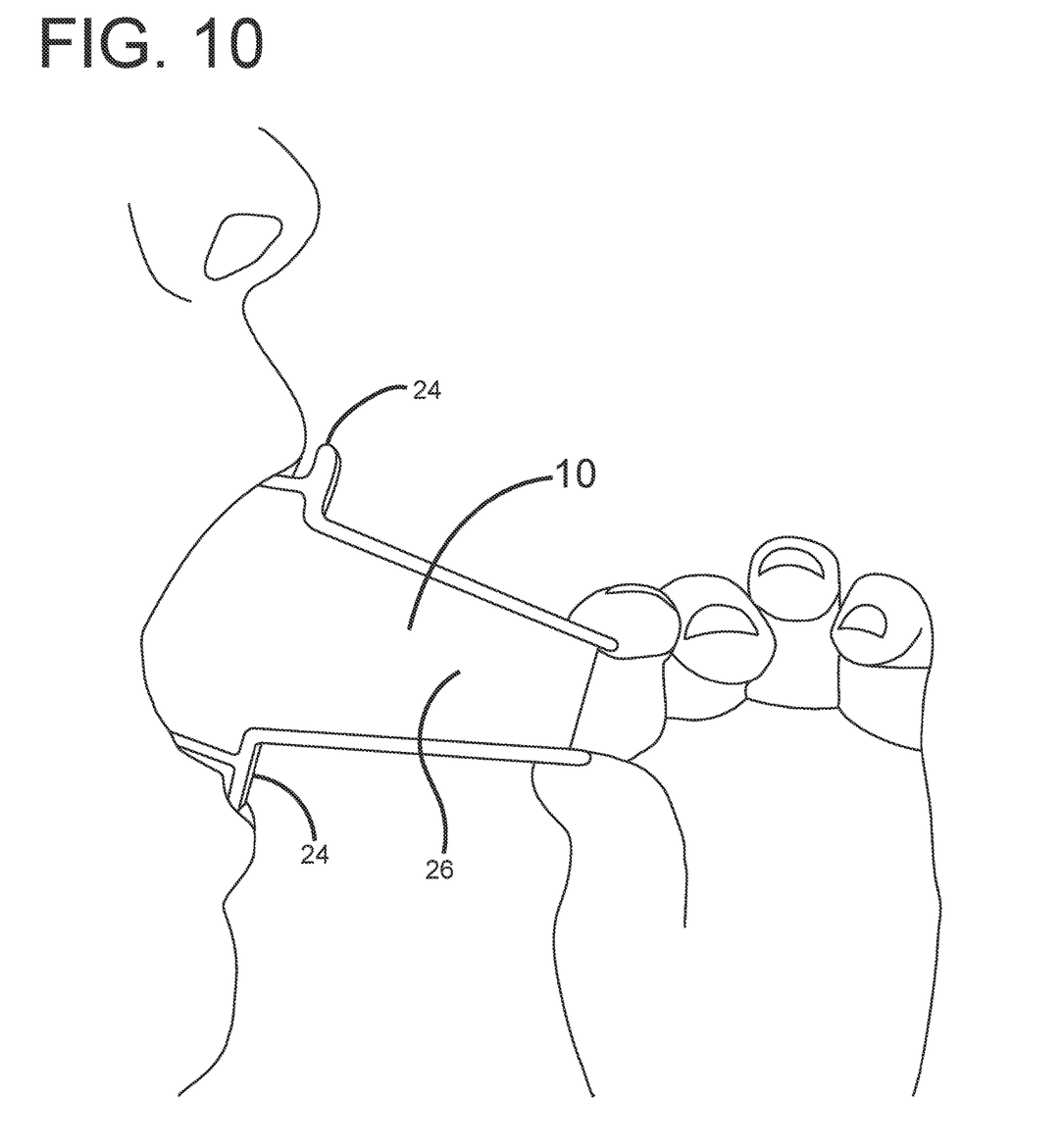
FIG. 10 shows an illustration of the disclosed mouth-opening measuring device inserted in a user's mouth to take a measurement.

The device 10 disclosed herein may be made from a variety of materials including, but not limited to plastics and polymers, such as polypropylene. As a result, the device 10 may be lightweight, durable, and soft for the inside and outside of a mouth. In one embodiment, it is noted that the truncated, substantially V-like geometry of device 10 facilitates the individual in prying open their mouth in order to insert and safely use the device. FIG. 10 shows a user 100 employing the user's hand 102 to insert device 10 into the user's mouth 104 to take a mouth-opening distance reading. During insertion and measurement reading, members 24 remain external to mouth as shown.

Figure 11:
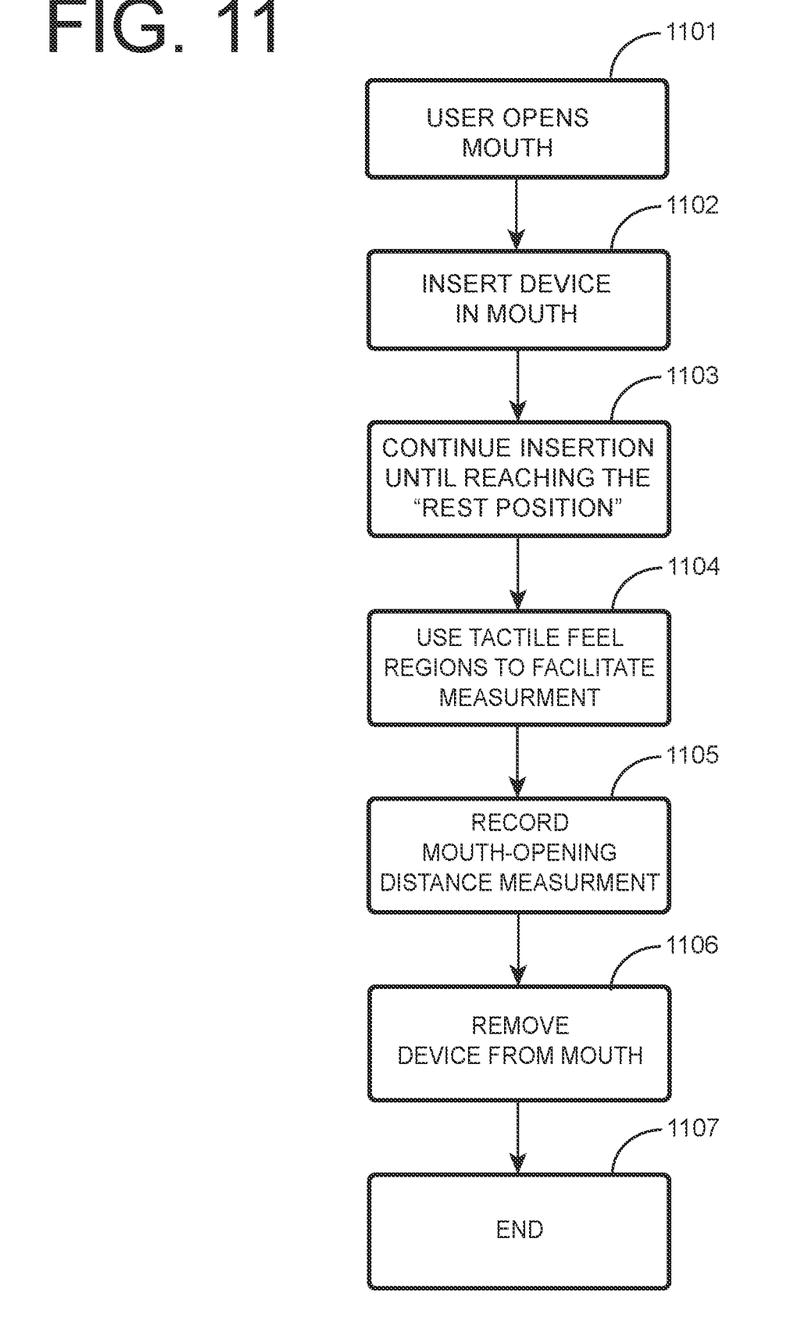
FIG. 11 shows a representative flowchart of a method of using the disclosed mouth-opening measuring device.

As seen in the flowchart of FIG. 11, a method of using the mouth-opening measuring device 10 to measure the opening between an upper jaw and a lower jaw commences with an individual opening their mouth, as per block 1101. Then, the device 10 is inserted into the individual's mouth, by either a medical practitioner or the individual, from either the first end 12 or the second end 14 of the device 10, as per block 1102. Next, the device 10 is inserted as far it can go in the mouth and the individual's teeth come to rest on either the first and second engagement portions 16, 18 or the third and fourth engagement portions 20, 22, depending on whether the first end 12 or the second end 14 was inserted into the individual's mouth, as per block 1103. This location is the "rest position". The extent of mouth opening can then be measured based on how far along either the first and second engagement portions 16, 18 or the third and fourth engagement portions 20, 22 the individual's teeth are found. The tactile regions (e.g. notches, bumps) 28 may be used as markers to correspond to specific measurements on the measuring surface 26 that are read by the individual or by a medical practitioner, as per block 1104. The mouth-opening distance measurement is recorded, as per block 1105. The device is removed from the mouth, as per block 1106 and the process ends, as per block 1107.

It is to be understood that the various embodiments described in this specification and as illustrated in the attached drawings are simply exemplary embodiments illustrating the inventive concepts as defined in the claims. As a result, it is to be understood that the various embodiments described and illustrated may be combined to form the inventive concepts defined in the appended claims.

In accordance with the provisions of the patent statutes, the present disclosure has been described to represent what is considered to represent the preferred embodiments. However, it should be noted that this disclosure can be practiced in other ways than those specifically illustrated and described without departing from the spirit or scope of this disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A device for measuring a mouth opening between an upper jaw and a lower jaw, the device comprising:
    a first end and an opposing second end, wherein the first end exhibits a width that is less than a width of the second end;
    a plurality of engagement members, each configured to be engaged with a tooth on the upper jaw and/or a tooth on the lower jaw, wherein each of the engagement members includes an inner surface and an outer surface;
    a measuring surface positioned between and connected with first and second engagement members, wherein the measuring surface includes a plurality of measurement values; and
    a plurality of tactile feel regions disposed along the outer surfaces of each of the engagement members, wherein the tactile feel regions are adjacent to and associated with corresponding measurement values on the measuring surface.

2. The device of claim 1, wherein the plurality of tactile feel regions comprises notches on the outer surfaces of each of the engagement members.

3. The device of claim 1, wherein the plurality of tactile feel regions comprises raised portions on the outer surfaces of each of the engagement members.

4. The device of claim 1, wherein the first and second engagement members exhibit a substantially truncated V-like geometry including a truncated portion at the first end of the device.

5. The device of claim 4, wherein the first and second engagement members angle away from one another from the first end of the device.

6. The device of claim 4, further comprising third and fourth engagement members that exhibit a substantially truncated V-like geometry including a truncated portion at the second end of the device.

7. The device of claim 6, wherein the third and fourth engagement members angle away from one another from the second end of the device.

8. The device of claim 7, wherein the device includes a middle from which first and second radially extending members extend.

9. The device of claim 8, wherein the first and second radially extending members are substantially perpendicular to the first, second, third and fourth engagement members.

* * * * *